(12) United States Patent
Sumner et al.

(10) Patent No.: US 9,926,576 B2
(45) Date of Patent: *Mar. 27, 2018

(54) PREVENTION OF BACTERIAL GROWTH IN FERMENTATION PROCESSES

(71) Applicant: E. I. DU PONT DE NEMOURS AND COMPANY, Wilmington, DE (US)

(72) Inventors: Eric Guy Sumner, Hockessin, DE (US); Derrick Okull, Wilmington, DE (US); Dwayne William Dischert, Middletown, RI (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 27 days.

This patent is subject to a terminal disclaimer.

(21) Appl. No.: 14/491,810

(22) Filed: Sep. 19, 2014

(65) Prior Publication Data

US 2015/0079653 A1    Mar. 19, 2015

Related U.S. Application Data

(63) Continuation of application No. 11/820,401, filed on Oct. 1, 2007, now abandoned.

(51) Int. Cl.
C12P 7/06 (2006.01)
C12N 1/20 (2006.01)
C12N 1/36 (2006.01)

(52) U.S. Cl.
CPC ............... *C12P 7/06* (2013.01); *C12N 1/20* (2013.01); *C12N 1/36* (2013.01); *Y02E 50/17* (2013.01)

(58) Field of Classification Search
None
See application file for complete search history.

(56) References Cited

U.S. PATENT DOCUMENTS

| | | |
|---|---|---|
| 2,701,781 A | 2/1955 | de Guevara |
| 3,082,146 A | 3/1963 | Wentworth et al. |
| 3,123,521 A | 3/1964 | Wentworth et al. |
| 3,271,242 A | 9/1966 | McNicholas |
| 3,278,447 A | 10/1966 | McNicholas |
| 3,585,147 A | 6/1971 | Gordon |
| 3,591,515 A | 7/1971 | Lovely |
| 4,104,190 A | 8/1978 | Hartshorn |
| 4,242,454 A | 12/1980 | Muller et al. |
| 4,355,108 A | 10/1982 | Gaddy et al. |
| 4,361,651 A | 11/1982 | Keim |
| 4,385,118 A | 5/1983 | Muller et al. |
| 4,419,448 A | 12/1983 | Kretz |
| 4,490,469 A | 12/1984 | Kirby et al. |
| 4,499,077 A | 2/1985 | Stockel et al. |
| 4,564,595 A | 1/1986 | Neves |
| 4,567,145 A | 1/1986 | Faber et al. |
| 4,689,215 A | 8/1987 | Ratcliff |
| 4,696,811 A | 9/1987 | Ratcliff |
| 4,808,389 A | 2/1989 | Ratcliff |
| 4,929,365 A * | 5/1990 | Clark ............. A01N 59/00 210/754 |
| 4,978,535 A | 12/1990 | Ractliff |
| 4,997,626 A | 3/1991 | Dziabo et al. |
| 5,075,117 A | 12/1991 | Kumami et al. |
| 5,165,910 A | 11/1992 | Oikawa et al. |
| 5,246,662 A | 9/1993 | Ripley et al. |
| 5,710,030 A | 1/1998 | Anderson |
| 6,363,734 B1 | 4/2002 | Aoyagi |
| 6,582,682 B2 | 6/2003 | Stier |
| 6,858,181 B2 | 2/2005 | Aoyagi |
| 6,946,021 B2 | 9/2005 | Aoyagi |
| 6,962,722 B2 | 11/2005 | Dawley et al. |
| 8,846,357 B2 * | 9/2014 | Leana ............. C12H 1/00 127/37 |
| 2006/1059812 | 7/2006 | Goodwin et al. |
| 2008/0206215 A1 | 8/2008 | Ziegler |
| 2011/0236257 A1 * | 9/2011 | Sumner .......... A01N 59/00 422/37 |

FOREIGN PATENT DOCUMENTS

| | | |
|---|---|---|
| CN | 1097716 | 1/1995 |
| CN | 1631770 | 6/2005 |
| JP | 60066973 | 4/1985 |
| JP | 2004/105431 | 4/2004 |
| WO | WO 2004/072291 | 8/2004 |
| WO | WO 2005/000368 | 1/2005 |
| WO | WO 2006/000756 | 1/2006 |

OTHER PUBLICATIONS

"Chlorine dioxide in the beverage industry", Pet Planet Insider, vol. 6, pp. 46-47, (2005). XP002507952.
Bothast, "Biotechnological processes for conversion of corn into ethanol", Appl. Microbiol. Biotechnol., 67: 19-25, (2005).
Chang, et al., "Bacterial contamination and its effects on ethanol fermentation", Journal of Microbiology and Biotechnology, vol. 5, No. 6, pp. 309-314, (1995).
Chang, et al., "Use of sulfite and hydrogen peroxide to control bacterial contamination in ethanol fermentation", Applied and Environmental Microbiology, vol. 63, No. 1, pp. 1-6, (1997).
Chen, et al., "Eradication of adherent bacteria on fish zygotes with stable chlorine dioxide, Huazhong Nongye Daxue Xuebao", 20(6): 568-570, (2001). Abstract.
Costlow, "Use of chlorine dioxide for controlling microorganisms during the handling and storage of fresh cucumbers", Journal of Food Science, 49(2): pp. 396-401, (1984).
Cravens, "Stabilized chlorine dioxide for controlling microorganisms", Papel, 40: 55-57, (1979).
De Oliva-Neto, et al., "Susceptibility of *Saccharomyces cerevisiae* and lactic acid bacteria from the alcohol industry to several antimicrobial compounds", Brazilian Journal of Microbiology, vol. 32, pp. 10-14, (2001). XP002507953.

(Continued)

*Primary Examiner* — Irene Marx

(57) ABSTRACT

A fermentation process for the production of ethanol from natural sources, such as corn, comprising introducing a fermentable sugar, an inoculant, and a stabilized chlorine dioxide into a fermentation system is disclosed. The stabilized chlorine dioxide is added preventatively to the fermentation system, at concentrations in the fermentation system of acetic acid no greater than 0.30% (weight/volume) and lactic acid no greater than 0.60% (weight/volume). The stabilized chlorine dioxide is added in an amount effective to substantially prevent growth of bacteria.

19 Claims, 1 Drawing Sheet

(56) References Cited

OTHER PUBLICATIONS

Delia-Dupuy, et al., "Contamination par les levures Brettanomyces dans les fermentations alcooliques", M.A.N. Microbiologie Aliments Nutrition, Le Plessis-Robinson, FR, vol. 13, pp. 349-359, (1995). XP002119778.

Elphick, "No nasty flavours from brewing with C102-dosed liquor", Brewing & Distilling International 1993 Prominent Fluid Controls (UK) Ltd, Swadlincote, Derbyshire, UK, vol. 24, No. 4, p. 37, (1993).

Erasmus, et al., "Impact of Yeast Strain on the Production of Acetic Acid, Glycerol, and the Sensory Attributes of Icewine", Am. J. Enol., 55: pp. 371-378, (2004).

Ethanol, Iowa Corn: Product descriptions. Copyright © 2007 Iowa Corn Promotion Board/ Iowa Corn Growers Association. http://www.iowacorn.org/ethanol/ethanol_11.html.

Felton, Ethanol, mouthwash, and cars?, Apr. 10, 2006. http://www.chemistry.org/portal/a/c/a/1/home/html.

Gibbons, et al., "Use of Potassium meta Bisulfite to control bacterial contaminants. During fermentation of fodder beet cubes for fuel ethanol", Biomass, 11, pp. 99-113, (1986).

Han, et al., "Efficacy of chlorine dioxide gas as a sanitizer for tanks used for aseptic juice storage", Food Microbiology, vol. 16, No. 1, pp. 53-61, (1999). XP00790622.

Hynes, et al., "Use of virginiamycin to control the growth of lactic acid bacteria during alcohol fermentation", Journal of Industrial Microbiology & Biotechnology, 18: pp. 284-291, (1997).

Kohl, Ethanol 101: Overview of Ethanol Production. Technical Connections, Ethanol Today (10-part series), Jul. 2003 through Jun. 2004.

Li, et al., "Study on stable unified disinfectant capable of releasing chlorine dioxide; Hunan Yike Daxue Xuebao", 24(3): 296-298, (1999).

Narendranath. N.V., Ph.D. Thesis, Department of Applied Microbiology and Food Science, University of Saskatchenwan, Saskatoon, 2000.

Ramirez-Orozco Martin, et al., "Debaryomyces hansenii growth in nonsterile seawter C102-peptone-containg medium", Canadian Journal of Microbiology, vol. 47, No. 7, pp. 676-679, (2001).

Saitoh, et al., "Genetically Engineered Wine Yeast Produces a High Concentration of L-Lactic Acid of Extremely High Optical Purity", Applied and Environmental Microbiology, vol. 71, No. 5, pp. 2789-2792, (2005).

Shui, et al., "Application of stable chlorine dioxide in malting and production of beer, Niangjiu", 2: 80-81, (1999). Abstract.

Skinner, et al., "Bacterial contaminants of fuel ethanol production", J. Ind. Microbiol., 31: 401-408, (2004).

Soeder, et al., VEROX®—8 cooling water treatment microbiocide—A comprehensive review of a stabilized chlorine dioxide technology presented before: Association of water technologies 2004 annual convention and exposition Gaylord Opryland resort and convention center Nashville, TN, Nov. 3-6, 2004.

* cited by examiner

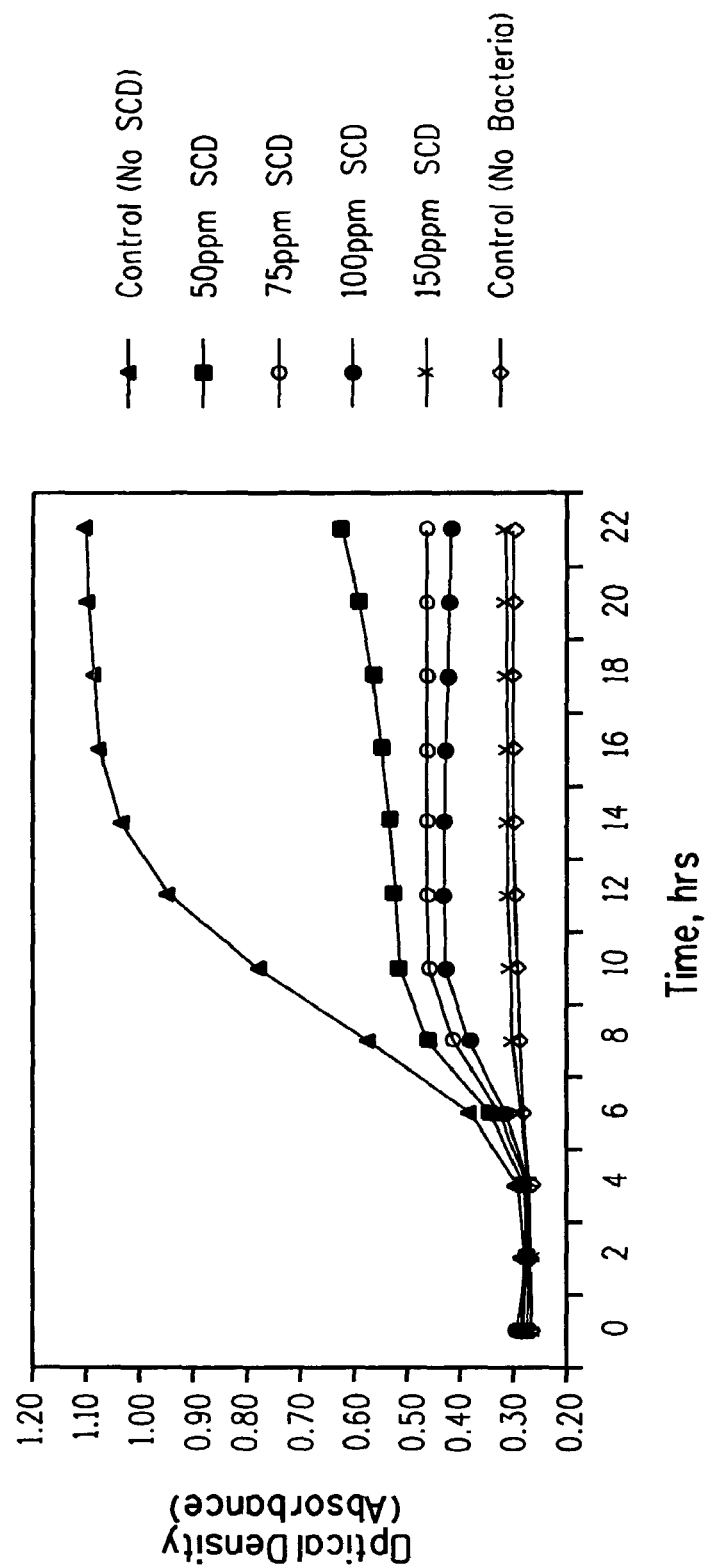

PREVENTION OF BACTERIAL GROWTH IN FERMENTATION PROCESSES

CROSS REFERENCE TO RELATED APPLICATIONS

The present application is a Continuation of U.S. application Ser. No. 11/820,401, filed Oct. 1, 2007, the disclosure of which application is incorporated herein in its entirety.

FIELD OF THE INVENTION

The present invention relates to a fermentation process to produce ethanol, specifically, a process wherein bacterial infection is substantially prevented.

BACKGROUND OF THE INVENTION

As petroleum reserves become depleted and more expensive, the need for alternative, and preferably sustainable, energy sources increases. For some years, ethanol has been considered and has been used as an option for partial or complete replacement of petroleum-based fuels for different applications. Ethanol-powered automobiles are a reality. Ethanol has advantages over the use of conventional gasoline as a renewable fuel source.

Ethanol is a major chemical product which has been produced by humans for millennia from natural sources. Currently ethanol is produced on a large scale from natural sources by a fermentation process in which sugar is converted to ethanol and carbon dioxide by yeast. Many feedstocks can be used to provide the sugar for fermenting. Current natural sources include corn, milo, wheat, barley, millet, straw, sorghum, sugar cane, sugar beets, molasses, whey, and potatoes. In fact, any starch or cellulosic material, which includes nearly all plants, can be used as a source of sugar for use in producing ethanol, as starch or cellulose can be a precursor to sugar.

An important concern with conventional fermentation systems is the difficulty in preventing microbial contamination, especially bacterial infection. Unfortunately, the optimum atmosphere for fermentation is also extremely conducive to bacterial growth. Bacteria can convert sugar (glucose) to organic acids, such as acetic acid and lactic acid, rather than ethanol. Furthermore, bacteria grow rapidly in the nutrient rich environment of a fermentation system, and may consume sugar (glucose) faster than does yeast. Furthermore, organic acids produced by the bacteria inhibit performance and growth of yeast. Thus, bacterial infection results in decreased yield of ethanol, and the fermentation process becomes less economical.

Current industry strategies to combat bacterial infection in fermentation systems include monitoring for the presence of organic acids (e.g., acetic acid and lactic acid) followed by remedial treatment. That is, once acids are detected, antibiotics or biocides may be added to control bacterial growth. However, bacterial growth and infection is a recurring problem. Any feed to a fermentation system, such as water, mash, enzymes and yeast as well as the fermenting vessel itself (if not disinfected between batches) can be a source of bacteria. Therefore, frequent monitoring is necessary and repeated introductions of antibiotics may be required.

Use of antibiotics to reduce bacterial growth in a fermentation system has become disfavored. Certain antibiotics remain and accumulate in solid products of fermentation, if they are not deactivated upon reaction with target bacteria. Solid products include distillers dried grain solids (DDGS) and distillers wet grain solids (DWGS). DDGS and DWGS are valuable byproducts of fermentation and are used in animal feeds. In many countries the amount of antibiotics in animal feed is under or being considered for regulatory control.

Generally, biocides perform poorly in fermentation systems, because they are non-specific and may also attack yeast. Stabilized chlorine dioxide (SCD) is a biocide that has been used in fermentation systems to treat bacterial infection. While yeast appears to be unaffected, this treatment is remedial, that is, only after the system has become infected. Repeated additions may also be required as indicated above.

U.S. Pat. No. 4,929,365 describes a remedial treatment process to remove microorganisms and biofilm produced by such microorganisms which then inhabit the biofilm, from a submerged substrate in an aqueous environment. The process uses stabilized chlorine dioxide (SCD), which is introduced to the substrate and allowed to penetrate through the protective biofilm and into the microorganism layer. A nutrient source is needed to create an acidic environment within the biofilm. This acidic environment activates the SCD, which in turn kills and destroys the microorganism and biofilm from the submerged substrate.

An alternative to remedial treatment is to prevent growth of bacteria. Addition of antibiotics in amounts to prevent growth of bacteria has been used. However, the issue of antibiotics accumulating in fermentation solids remains. Development of bacterial resistance is also a well known consequence of antibiotic use.

Thus, there is a need to prevent bacterial growth in a fermentation process, while minimizing or eliminating the use of antibiotics. The present invention meets this need.

SUMMARY OF THE INVENTION

The present invention provides a process to substantially prevent the growth of bacteria in a fermentation system comprising introducing a fermentable sugar, an inoculant and a stabilized chlorine dioxide into a fermentation system wherein the inoculant converts the sugar to ethanol and carbon dioxide; and wherein the stabilized chlorine dioxide is added, in an amount effective to substantially prevent growth of bacteria, to one or more of the fermentable sugar, the inoculant, or the fermentation system at concentrations in the fermentation system of acetic acid no greater than 0.30% (weight/volume) and lactic acid no greater than 0.60% (weight/volume). The stabilized chlorine dioxide comprises at least one of a chlorine dioxide-containing oxy-chlorine complex, a chlorite-containing component, or an entity capable of forming chlorine dioxide in a liquid medium when exposed to acid. The amount of stabilized chlorine dioxide added is from about 0.0001 to about 5%, based on the weight of activated chlorine dioxide which can be produced and the total weight of the fermentation system.

The stabilized chlorine dioxide can be added to one or more of the fermentable sugar, the inoculant, or the fermentation system, in an amount effective to substantially prevent growth of bacteria and thus formation of organic acids in the system. Preferably the stabilized chlorine dioxide is added to the fermentation system before addition of fermentable sugar or before addition of inoculant to the fermentation system, more preferably before addition of the inoculant.

BRIEF DESCRIPTION OF THE DRAWING

FIG. 1 shows the optical density of bacterial cells suspended in liquid growth medium; stabilized chlorine dioxide was added to growth medium containing the cells at increasing concentrations, and optical density was monitored for a period of 22 hours.

DETAILED DESCRIPTION OF THE INVENTION

The present invention relates to the industrial production of ethanol via fermentation. The following is a description of how this process may be performed using corn as the feedstock. It will be understood by those skilled in the art this process may be varied, e.g., by use of other feedstocks.

Ethanol can be produced from corn or other grain in wet mill and dry mill processes as are known to those skilled in the art. In a wet mill process, corn is soaked or steeped and then separated into components. In a dry mill process, corn is ground into meal and processed without separation. The corn starch component from the wet mill process or meal from the dry mill process is mixed with water and enzymes and cooked to solubilize the starch.

Corn starch is a polysaccharide, that is, a polymer, made of individual units of glucose. Starch is converted to smaller (shorter) polysaccharides, i.e., dextrins, by enzymes (α-amylase). The smaller polysaccharides are converted to a fermentable sugar, that is, glucose (monosaccharide), using the enzyme glucoamylase.

The process to produce ethanol then comprises fermenting the sugar in a batch or continuous reactor by contacting the sugar with an inoculant, such as yeast, in a fermentation system, to produce a fermentation product comprising ethanol and carbon dioxide. Subsequent steps include distilling the fermentation product to remove about 95% of the liquid, as well as the solids and produce a distilled ethanol comprising about 5% water; and dehydrating the distilled ethanol, thereby producing 100% (200 proof) ethanol. Additional steps comprise denaturing the dried ethanol by mixing in about 2-5% gasoline or other additive for non-liquor uses; and recovering co-produced carbon dioxide and solids. Additional steps in beverage ethanol production may include aging, blending, and bottling such as those described in U.S. Patent Application 20060159812A1. Such additional steps are also described in Kirk-Othmer Encyclopedia of Chemical Technology, "Beverage Spirits, Distilled" by John E. Bujake, John Wiley & Sons, Inc. (New York), 2001. These steps are known to those skilled in the art.

Processes for the production of ethanol are performed under conditions which do not preclude introduction of bacteria to fermentation systems. Sources of bacteria in a fermentation system may include any of the feeds (fermentable sugar, inoculant) introduced into the system. Inadequate cleaning of fermentation systems between batches or runs may also be a source of bacteria for subsequent fermentations. Bacterial infections of fermentation systems produce byproduct organic acids from the fermentable sugar, particularly acetic acid and lactic acid. Thus, bacteria consume ingredients (fermentable sugar) and inhibit activity of the inoculant. Acetic acid and lactic acids are also produced by yeast during fermentation, but in amounts not sufficient to significantly interfere with the overall yield and efficiency of the process, as described herein. Increasing concentrations of the organic acids indicates growth of bacterial infection in a fermentation system.

In the process of the present invention, stabilized chlorine dioxide (SCD) is added to one or more of the fermentable sugar, the inoculant, or the fermentation system, in an amount effective to substantially prevent growth of bacteria and thus formation of organic acids in the system. That is, SCD is added prior to substantial growth of bacteria in the system, such as prior to the introduction of any or all of the ingredients necessary to initiate the fermentation process, or as can be determined by concentrations of acetic acid and lactic acid in the system. Bacteria are thus substantially prevented from growing in the fermentation system in the presence of the SCD. Surprisingly, SCD remains in the fermentation system and bacteria are substantially prevented from growing and contaminating the product through in situ generation of activated chlorine dioxide, that is, $ClO_2$, by reaction of SCD with acid produced in the system.

In order to substantially prevent growth of bacteria and significant formation of organic acids in a fermentation system, stabilized chlorine dioxide is added at concentration of acetic acid of no greater than 0.30% (weight/volume) and at concentration of lactic acid of no greater than 0.60% (weight/volume). At acid concentrations above these levels, there is significant deleterious effect on the yeast and significant loss of ethanol yield based on conversion of sugar. Thus, the addition of stabilized chlorine dioxide above these levels would be remedial, since significant bacterial growth has already occurred, as indicated by the concentrations of the organic acids.

Fermentable Sugar

A fermentable sugar suitable for use in this invention can be derived from essentially any plant source comprising sugar, starch and/or cellulose. That is, starch and/or cellulose can be converted by processes known in the art, e.g., using enzymes, to sugar suitable for use as a fermentable sugar in this invention. The fermentable sugar can be derived from one or more of any grain-based product such as corn, wood chips, wheat straw, corn stover, switch grass. The fermentable sugar may alternatively be derived from milo, barley, millet, sorghum, sugar cane, sugar beets, molasses, whey, potatoes. Processes are known to those skilled in the art to convert these sources to fermentable sugar. Conveniently, the fermentable sugar is derived from corn, using either the wet mill or dry mill process to produce a liquefied starch. The liquefied starch undergoes saccharification, in which the starch is contacted with enzymes to convert the starch to glucose, thus forming the fermentable sugar.

The term "mash" is used to herein to refer to a composition comprising a fermentable sugar. Mash includes any mixture of mixed grain or other fermentable carbohydrates in water used in the production of ethanol at any stage from mixing of the fermentable sugar in water to prior to any cooking and saccharification through to completion of fermentation, as defined in Jacques, K. A., Lyons, T. P., Kelsall, D. R, "The Alcohol Textbook", 2003, 426-424, Nottingham University Press, UK.

In a fermentation process, sugar is typically present in the fermentation system in a concentration of about 5 to about 40% (weight/volume), preferably in the range of about 10 to 35% (weight/volume).

Inoculant

For purposes herein, an inoculant is a microorganism which is capable of converting a fermentable sugar to ethanol. Yeasts are common inoculants, which are used in ethanol fermentation. Yeasts are microorganisms capable of living and growing in either aerobic (with oxygen) or anaerobic (lacking oxygen) environments.

The following discussion is directed to a process in which the inoculant is yeast.

Relative to bacteria, yeasts may have moderate to slow fermentation rates. To compensate for their metabolic rate, large amounts of yeast may be required in large scale industrial ethanol production. Prior to introducing yeast into a fermenting vessel, a yeast inoculum is produced in a propagation tank separate from the fermenting vessel. In a propagation tank, a yeast starter culture is supplied with nutrient composition, which may comprise fermentable sugar, enzymes, and water to activate or grow the yeast. Yeast propagation also occurs during the fermenting step. However, activation of yeast in a propagation tank provides highly active yeast upon introduction to the fermenting vessel.

Inoculant yeast is added to the fermentation system in an amount typically about 1 pound of dry yeast per 1000 gallons (1 kilogram per 8000 liters) of composition comprising fermentable sugar, that is, mash. Typical holdup times for the fermenting step at this loading of yeast are between 40 and 72 hours. It will be recognized by those skilled in the art that the amount of yeast added may vary, along with holdup times.

Stabilized Chlorine Dioxide

The term "stabilized chlorine dioxide" as used herein means one or more chlorine dioxide-containing oxy-chlorine complexes and/or one or more chlorite-containing components and/or one or more other entities capable of forming chlorine dioxide in a liquid medium in when exposed to acid. Thus, stabilized chlorine dioxide comprises at least one of a chlorine dioxide-containing oxy-chlorine complex, a chlorite-containing component, or an entity capable of forming chlorine dioxide in a liquid medium when exposed to acid. In the present invention, stabilized chlorine dioxide reacts with an organic acid, such as acetic acid and/or lactic acid, e.g., produced by contaminating bacteria. When activated by acid, chlorine dioxide is a wide spectrum biocide, capable of eliminating the deleterious impact of the contaminating bacteria in a fermentation system. Stabilized chlorine dioxide may also be referred to as "chlorine dioxide precursor" or abbreviated herein as "SCD".

Among the preferred chlorine dioxide-containing oxy-chlorine complex is selected from the group consisting of complex of chlorine dioxide with carbonate, complex of chlorine dioxide with bicarbonate and mixtures thereof. Examples of chlorite-containing components include metal chlorites, and in particular alkali metal and alkaline earth metal chlorites. A specific example of a chlorite-containing component which is useful as a chlorine dioxide precursor is sodium chlorite, which can be used as technical grade sodium chlorite. The exact chemical composition of many of stabilized chlorine dioxide, and in particular, chlorine dioxide complexes, is not completely understood. The manufacture or production of certain chlorine dioxide precursors is described by Gordon, U.S. Pat. No. 3,585,147 and Lovely, U.S. Pat. No. 3,591,515. Specific examples of useful stabilized chlorine dioxide include, for example, ANTHIUM DIOXCIDE, available from International Dioxcide Inc., North Kingstown, R.I.; OXINE and PUROGENE, available from Bio-Cide International, Inc., Norman, Okla.

The stabilized chlorine dioxide (chlorine dioxide precursor), SCD, may be provided in a liquid medium at a predetermined concentration, e.g., a concentration chosen to provide a disinfecting amount of chlorine dioxide in response to at least one factor other than the presence of the organic acids to be reduced. Preferably, the liquid medium has sufficient SCD so as to have a potential concentration of chlorine dioxide in the range of about 0.002% to about 40% by weight, preferably, in the range of about 2% to about 25% by weight, more preferably in the range of about 5% to about 15% by weight, based on the total weight of the liquid medium including the chlorine dioxide-containing complexes and/or one or more chlorite-containing components and/or one or more other entities capable of forming chlorine dioxide.

The stabilized chlorine dioxide may be provided as a solid material, such as a composition comprising an alkali or alkaline earth metal chlorite powder, inert ingredients, and optionally dry activator such as a dry acid. Preferably the metal chlorite is an alkali metal chlorite, more preferably sodium chlorite.

Stabilized chlorine dioxide is activated in situ by lowering pH to less than pH 8, for example by adding acid, metals and/or by in situ acid production, e.g., from certain acid-producing bacteria. The lower the pH, the faster the SCD is activated. For purposes herein, the SCD remains inactive in the solution until acid is generated, which converts the SCD to activated chlorine dioxide. The more acids generated, the more activated chlorine dioxide is produced. Activated chlorine dioxide destroys bacteria by reacting with a number of cellular components (proteins, lipids, etc.). Since chlorine dioxide attacks multiple sites on or in a cell, resistance is unlikely to occur, a known problem with antibiotics.

Process

The present invention is a process to substantially prevent the growth of bacteria in a fermentation system comprising introducing a fermentable sugar, an inoculant, and a stabilized chlorine dioxide into a fermentation system. The SCD is added at concentrations in the fermentation system of acetic acid no greater than 0.30% (weight/volume) and lactic acid no greater than 0.60% (weight/volume) in an amount effective to substantially prevent growth of bacteria. It is known to those skilled in the art that acetic acid and lactic acid may be present in small amounts in a fermentation system, that is, without substantial bacterial growth. These organic acids can form as a byproduct of fermentation of sugar by yeast. In the event exposure of SCD to small amounts of acid generates activated chlorine dioxide, there is substantially no adverse effect on the inoculant (e.g., yeast), fermentation process and ethanol yield.

SCD may be added to the fermentable sugar or to the inoculant prior to their introduction into the fermentation system. The fermentation process may be either batch or continuous. By "fermentation system", it is meant herein to refer to the batch or continuous flow liquefaction train and fermentation tanks, vessels, reactors, heat exchangers, piping (such as a plug flow reactor) or combinations thereof in which the fermentation of sugar occurs. Alternatively or in addition, SCD may be added as a separate stream to the fermentation system, apart from the fermentable sugar and inoculant. In a batch process, the SCD may alternatively be added before, during and/or following the addition of the fermentable sugar and/or inoculant to the fermentation system. When the inoculant is yeast, SCD may be added to the yeast propagation tank. Preferably, the SCD will be added before addition of fermentable sugar or before addition of inoculant to the fermentation system to gain the best results. Most preferably, the SCD is added before addition of inoculant, especially when the inoculant is yeast. SCD should be added to the fermentable sugar, inoculant or fermentation system at concentrations in the system of acetic acid no greater than 0.30% (weight/volume) and lactic acid no greater than 0.60% (weight/volume). At these concentrations of acid there is no substantial deleterious effect on the fermentation process from bacteria.

Stabilized chlorine dioxide is added in an effective amount. By "effective amount" is meant an amount that is capable of generating sufficient activated chlorine dioxide in the fermentation system to substantially prevent growth of bacteria without adversely affecting the fermentation process. By "substantially prevent growth of bacteria", it is meant that concentration in the fermentation system of acetic acid is no greater than 0.30% (weight/volume) and concentration of lactic acid no greater than 0.60% (weight/volume) acid. Such conditions allow the inoculant to quickly and effectively convert the fermentable sugar to ethanol. Thus, in the process of this invention, there is a reduction in acid production relative to operating in the absence of an effective amount of stabilized chlorine dioxide. Furthermore, in the process of this invention there is also a reduction in acid production and increase in ethanol production relative to remedial treatment with SCD in an infected process. In remedial treatment, acid production and ethanol yield loss occur before the added remedial SCD takes effect. In the process of this invention, relative to remedial treatment, there is also minimal loss in cycle time, or ethanol yield.

Stabilized chlorine dioxide is added in an amount effective to substantially prevent the growth of bacteria but have little impact on the major variables in the fermentation process. This amount will typically be from about 0.0001 to about 5% based on the weight of activated chlorine dioxide which can be produced and total weight of the contents of the fermentation system—when all of the reactants have been added to the system. It will be understood that the amount of SCD needed will depend on the total bacteria load introduced to the system. Additional factors to consider in determining the amount of SCD to add include timing of inoculant (yeast) addition and pH. Preferably the amount of SCD added is about 0.01 to about 3%, more preferably, about 0.1 to about 2% of the total volume of material in the fermentation vessel. This amount is substantial enough to minimize process interruptions due to bacterial contamination, and to eliminate the need for other biocide or antibiotic. It will be understood by those skilled in the art that the concentration of SCD introduced into the fermentation process may vary depending on the concentration of dissolved chlorine dioxide available in the solution of SCD being added.

By operating a fermentation plant in accordance with this invention, a reduced rate in frequency of, with potential elimination of, deleterious effects of bacterial infection is achieved. Thus, in the process of this invention, long term productivity and profitability increase in the operation of a fermentation plant.

It is recognized that individual results at different ethanol fermentation plants operating under different conditions may vary in the relative improvements in the process of this invention, such as, in the reduction of acid production and increases in ethanol production relative to the absence of SCD or relative to the addition of remedial SCD.

In the process of this invention, fermentation occurs in a batch or continuous fermentation system. The product mixture from the fermentation system comprises ethanol, water, inoculant, grain solids and un-reacted SCD. After discharge from the fermentation system, conventional process steps for separation and purification or other processing of the ethanol may be performed. The fermentation product may be distilled to separate the ethanol from the bulk of the water present and from the solids (which include inoculants and grain solids). The solids may be recovered. The distilled ethanol may be further treated, for example by contacting with molecular sieves, to remove remaining water, so that the ethanol product is essentially 100% pure ethanol (200 proof). In beverage production, aging, blending or other processing may be required. Purified fuel ethanol is generally treated with a denaturing agent. Co-produced carbon dioxide and solids can also be recovered.

The recovered solids can be used in animal feed and mixed with distiller grains. Advantageously, the recovered solids, comprise SCD, which, when added to wet distiller grains, can extend their shelf life. Other advantages, such as odor/control, may also be achieved.

EXAMPLES

In the following examples, the stabilized chlorine dioxide that was used was ANTHIUM DIOXCIDE, available from International Dioxcide Inc., North Kingstown, R.I., as a solution containing 5% chlorine dioxide when activated.

Total viable bacteria in the samples herein was measured as a concentration of colony forming units (CFU) per unit of volume (i.e., CFU/ml) or per unit of mass (i.e., CFU/g) of sample (Example 1 and Example 2), or based on optical density readings using a spectrometer (Example 3). Optical density as measured using the spectrophotometer represents the amount of light of specific wavelength (450 nm) absorbed by bacterial cells and is directly proportional to the concentration of bacteria in the sample. That is to say, the higher the concentration of cells in the suspension, the higher the optical density of the sample, and vice versa. When used to compare bacterial cells exposed to varying conditions, lower optical densities indicate inhibition of bacterial growth. It is also understood that there is a direct correlation of concentration of bacteria in the samples and the CFU measurement. Thus, the higher the concentration of bacteria, the higher the CFU and vice versa. As a convention, CFUs are transformed mathematically into logarithmic values ($Log_{10}$ CFU) to simplify comparisons between different treatments.

Example 1

Samples of mash collected from a commercial ethanol processing plant provided the fermentable sugar used in this example. The samples were collected from the process stream immediately after the liquefaction, just prior to the introduction of inoculant (yeast) or any of the other ingredients (urea, enzymes, antibiotics) into the system. Samples were stored in a refrigerator at a temperature of 4° C. (39° F.) for five days prior to testing. The mash samples were exposed to varying concentrations of stabilized chlorine dioxide (SCD) as follows: 25 ml of the mash were transferred into 50 ml centrifuge tubes, which were then warmed to 33° C. (92° F.) in a water bath. SCD was added into the mash samples to achieve concentrations of chlorine dioxide in the mash of 62.5 ppm, 75 ppm, 100 ppm, 150 ppm, and 250 ppm. In a control sample, no SCD was added to the mash.

The treated samples and control sample were held in the water bath for 30 minutes, after which surviving bacteria were enumerated using standard microbiological methods. These methods entail the dilution of each sample by a factor large enough to enable clear separation of individual bacterial colonies on solid growth medium, herein referred to as dilution factor, thus allowing the colonies to be individually counted. In this example the growth medium was MRS agar, available from Difco Laboratories, Sparks, Md., on which organic acid producing bacteria are known to grow. Standard methods also entail the incubation of agar plates onto which diluted samples have been deposited/spread. In this example, the plates were incubated at 33° C. for 48 hours. Experiments were performed in duplicate. Results are provided below in Table 1. Count 1 and Count 2 indicate bacterial colony counts in each of the duplicate experiments. Mean is based on Count 1 and Count 2.

TABLE 1

Viable Bacteria Recovered from Mash Samples after Exposure to SCD for 30 minutes

| Concentration of SCD in mash | Count 1 | Count 2 | Mean | Dilution Factor | CFU/ml | Log CFU/ml |
|---|---|---|---|---|---|---|
| (Control) 0 ppm | 704 | 900 | 802 | 10000 | 80200000 | 7.9 |
| 62.5 ppm | 40 | 89 | 64.5 | 10000 | 6450000 | 6.81 |
| 75 ppm | 320 | 270 | 295 | 10000 | 2950000 | 6.47 |
| 100 ppm | 200 | 360 | 280 | 10000 | 2800000 | 6.45 |
| 150 ppm | 26 | 28 | 27 | 100 | 2700 | 3.43 |
| 250 ppm | 25 | 29 | 27 | 10 | 270 | 2.43 |

The number of viable bacteria in mash treated with the SCD was lower than untreated mash samples. Higher loadings of SCD resulted in less bacteria in the samples.

Example 2

During a normal fermentation process at dry-grind ethanol plant, two hundred and seventy (270) gallons (1000 liters) of SCD were added into a fermenter just prior to filling with mash, and prior to the addition of yeast, enzymes, and urea into the fermenter. No antibiotic compounds were added into the fermenter. In this process, the fermenter was filled with mash flowing at 660 gallons per minute up to a volume of 660,000 gallons. The concentration of SCD added into the vessel therefore varied as the volume of mash increased. That is, as filling began, the SCD was gradually diluted up to a final concentration of 0.041%. The SCD used in this example was a solution containing 5% active chlorine dioxide. 3500 gallons (28000 liters) of yeast suspension in mash containing approximately $1.0 \times 10^8$ cells per ml was added from the yeast propagation tank after 90 minutes of filling. When all components had been added into the fermentation vessel, the concentration of antibiotic (Virginiamycin) and urea were 0.0001% and 0.0016%, respectively. Fermentation performance indicators were monitored as usual and are shown in Table 2. Data was collected from fermentation batches running concurrently under each condition and the means calculated. Table 2 represents the means of 16 batch fermentations using antibiotics and 15 batch fermentations into which SCD was added.

TABLE 2

Key parameters for Batch Fermentations

|  | pH | Temp. (° C.) | Sugars, % | Lactic Acid, % | Glycerol, % | Acetic Acid, % | Ethanol, % |
|---|---|---|---|---|---|---|---|
| Antibiotic Treated |||||||  |
| Inoculant | 5.38 | 37 | 9.10 | 0.07 | 0.39 | 0.02 | 0.74 |
| 10 hours | 5.47 | 33 | 23.53 | 0.18 | 0.80 | 0.03 | 1.32 |
| 22 Hours | 4.81 | 32 | 11.54 | 0.28 | 1.46 | 0.02 | 7.53 |
| 36 Hours | 4.76 | 30 | 3.94 | 0.32 | 1.67 | 0.03 | 11.64 |
| Drop | 4.91 | 29 | 1.14 | 0.35 | 1.72 | 0.05 | 13.81 |
| SCD Treated |||||||  |
| Inoculant | 5.39 | 37 | 8.94 | 0.07 | 0.40 | 0.02 | 0.92 |
| 10 Hours | 5.60 | 33 | 24.70 | 0.15 | 0.75 | 0.03 | 1.00 |
| 22 Hours | 4.84 | 33 | 13.69 | 0.23 | 1.40 | 0.01 | 6.53 |
| 36 Hours | 4.74 | 29 | 5.75 | 0.25 | 1.66 | 0.02 | 10.91 |
| Drop | 4.88 | 29 | 1.14 | 0.25 | 1.77 | 0.04 | 14.08 |

As can be seen from Table 2, average ethanol yield at the end of the fermentation (Drop) for the SCD-treated fermentation was higher than antibiotic treated. Average lactic and acetic acid concentration were also lower for the SCD-treated fermenter. Thus, use of SCD rather than antibiotic increases ethanol yield, so that in a 56 million gallon (212 million liters) per year ethanol plant, an additional 1.1 million gallons (4.2 million liters) per year are produced. At a price of $2.20 per gallon the increased production represents additional annual review of $2.35 million.

Example 3

Pure cultures of lactic acid producing bacteria were isolated and identified from samples of mash obtained previously from a commercial fermentation process. Three of the isolates that had most frequently been identified were combined into a cocktail and exposed to increasing concentrations of SCD in MRS broth (Difco, Sparks, Md., USA), a selective medium for lactic acid producing bacteria. The species used were *Pediococcus pentosaceus*, *Lactobacillus sakei*, and *Leuconostoc citreum*. The three isolates were grown overnight on MRS agar, then washed off with a phosphate buffer, (pH 6.4), mixed and the total cell density was adjusted with the buffer to result in approximately $10^4$ CFU/ml of viable cells in a liquid growth medium. The cell suspension in the liquid medium was combined with SCD at concentrations of active chlorine dioxide of 50 ppm, 75 ppm, 100 ppm, and 150 ppm in 96-well micro-titer plates.

The optical density readings from each well were recorded at 2 hour intervals for 22 hours using an automated micro-titer plate reader. The optical density was measured using a spectrometer. Optical density indicates the concentration of bacterial cells in the medium. Higher turbidity of the samples indicates high concentration of the bacteria in the medium.

Bacteria exposed to various levels of SCD exhibit lower optical densities compared to untreated cells over the same 22-hour time period. FIG. 1 illustrates that by including SCD in the growth medium, the concentration of bacteria can be lowered and their rate of growth controlled, as measured by the optical density of the suspension.

What is claimed is:

1. A process to substantially prevent the growth of acid-producing bacteria in a fermentation process for the production of ethanol performed in a batch or continuous fermentation system, the fermentation system comprising a fermentation tank, vessel, reactor or piping, and the fermentation process comprising introducing a fermentable sugar, a yeast inoculant and a stabilized chlorine dioxide into the fermentation system; wherein the yeast inoculant converts the sugar to ethanol and carbon dioxide; wherein the stabilized chlorine dioxide is introduced when concentration in the fermentation system of acetic acid is no greater than 0.30% weight/volume, and concentration of lactic acid is no greater than 0.60% weight/volume;

wherein the acetic acid and lactic acid are by-products of the bacterial infection; wherein the amount of stabilized chlorine dioxide added is from about 0.0001 to about 5%, based on the total weight of the contents of the fermentation system; wherein the stabilized chlorine dioxide has no adverse effect on the yeast inoculant or ethanol yield; wherein the concentration in the fermentation system of acetic acid remains no greater than 0.30% weight/volume, and the concentration of lactic acid remains no greater than 0.60% weight/volume during the fermentation process, and wherein the stabilized chlorine dioxide is activated by in situ acid production.

2. The process of claim 1 wherein the stabilized chlorine dioxide is added to the fermentable sugar.

3. The process of claim 1 wherein the stabilized chlorine dioxide is added to the inoculant.

4. The process of claim 1 wherein the stabilized chlorine dioxide is added to the fermentation vessel.

5. The process of claim 1 wherein the stabilized chlorine dioxide is added in an amount from about 0.01% to about 3%.

6. The process of claim 5 wherein the stabilized chlorine dioxide is added in an amount from about 0.1% to about 2%.

7. The process of claim 1 wherein the stabilized chlorine dioxide is a chlorine dioxide-containing oxy-chlorine complex which is a complex of chlorine dioxide with carbonate, chlorine dioxide with bicarbonate or a mixture thereof.

8. The process of claim 1 wherein the stabilized chlorine dioxide is one or more metal chlorites.

9. The process of claim 8 wherein the metal chlorite is an alkali metal chlorite or an alkaline earth metal chlorite.

10. The process of claim 8 wherein the metal chlorite is sodium chlorite.

11. The process of claim 1 wherein the yeast inoculant is added in an amount of about 1 pound of dry yeast per 1000 gallons of composition comprising fermentable sugar.

12. The process of claim 1 wherein the fermentable sugar is derived from one or more of corn, wood chips, wheat straw, corn stover, switch grass, milo, barley, millet, sorghum, sugar cane, sugar beets, molasses, whey, and potatoes.

13. The process of claim 12 wherein the fermentable sugar is derived from corn.

14. The process of claim 13 wherein the fermentable sugar is present in the fermentation system in a concentration of about 5 to about 40% weight/volume.

15. The process of claim 14 wherein the fermentable sugar is present in the fermentation system in a concentration in the range of about 10 to 35% weight/volume.

16. The process of claim 1 wherein the stabilized chlorine dioxide is added to the fermentation system prior to addition of the inoculant.

17. The process of claim 1 wherein the stabilized chlorine dioxide is introduced before or simultaneously with the fermentable sugar and/or the yeast inoculant.

18. The process of claim 1 wherein the stabilized chlorine dioxide is added in an amount from about 0.002% to about 5%.

19. The process of claim 1 wherein the stabilized chlorine dioxide is added in an amount from about 0.005% to about 5%.

* * * * *